United States Patent [19]
Kleeman

[11] Patent Number: 4,995,274
[45] Date of Patent: Feb. 26, 1991

[54] LOCKING PIN AND NUT COMBINATION AND METHOD FOR VISUAL INSPECTION THEREOF

[76] Inventor: Henry Kleeman, Box 191, Oakville, Manitoba, Canada, R0H 0Y0

[21] Appl. No.: 438,041

[22] Filed: Nov. 20, 1989

[51] Int. Cl.$^5$ .................. G01N 21/29; G01M 11/00; F16B 39/04; F16B 41/00
[52] U.S. Cl. .................. 73/865.8; 73/865.9; 411/320
[58] Field of Search .......... 73/865.8, 865.9; 411/190–336

[56] References Cited

U.S. PATENT DOCUMENTS

| 1,119,613 | 12/1914 | Jazek | 411/320 |
| 1,858,039 | 5/1939 | Cooke | 411/320 |
| 2,307,919 | 1/1943 | Crabbs | 411/315 |
| 2,393,519 | 1/1946 | Crowther | 411/320 |
| 3,435,869 | 4/1969 | Ohlbaum | 411/320 |
| 3,638,980 | 2/1972 | Kleinhenn | 411/320 |
| 3,664,195 | 5/1972 | Fournier et al. | 73/865.8 |
| 4,125,008 | 11/1978 | Genest et al. | 70/135 X |
| 4,172,524 | 10/1979 | Holm et al. | 250/223 B X |
| 4,708,359 | 11/1987 | Davenport | 280/477 |
| 4,904,132 | 2/1990 | Popenoe | 411/13 |

FOREIGN PATENT DOCUMENTS

| 691756 | 10/1930 | France | 411/320 |
| 113906 | 9/1980 | Japan | 73/865.9 |
| 263965 | 2/1970 | U.S.S.R. | 73/865.9 |
| 228002 | 1/1925 | United Kingdom | 411/190 |
| 796096 | 6/1958 | United Kingdom | 411/190 |

Primary Examiner—Tom Noland
Attorney, Agent, or Firm—Adrian D. Battison; Stanley G. Ade; Murray E. Thrift

[57] ABSTRACT

Visual inspection of an assembly of a type including nuts and associated locking pins is improved by providing a visually distinctive color difference on the surface of the pin. The invention is particularly useful in assemblies such as air craft where there are a large number of castellated nuts which are located in place on the corresponding bolt by a cotter pin. The presence of the cotter pin can thus be visually determined more easily by its distinctive color from the corresponding castellated nut.

8 Claims, 1 Drawing Sheet

LOCKING PIN AND NUT COMBINATION AND METHOD FOR VISUAL INSPECTION THEREOF

BACKGROUND OF THE INVENTION

This invention relates to an arrangement including a nut and a locking pin therefor together with a method of visual inspection thereof.

Many assemblies in highly complex machines, for example, air craft include a large number of elements which are connected together. One common technique for fastening one element to another is to use a male threaded bolt or member on which a female screw threaded nut is placed and generally tightened. To prevent the nuts from becoming loosened during vibration, often a locking pin is applied to the combination to prevent the nut from rotating relative to the member except when the pin is removed.

In many cases, the nut is of the castellated type with the bolt member having a transverse hole so that the pin can extend between the castellations and through the hole to hold the nut against rotation.

Conventionally, a simple split pin is used which includes a pair of legs interconnected at one end of the pin by a loop member so the legs can pass through the hole in the bolt member and between the castellations and the loop member is received within the castellations following which the legs are bent apart to hold the device in place.

As will be apparent, devices of this type are used very widely in all types of different equipment.

Inspection of such equipment is in many cases mandatory and must be carried at regular intervals. The absence of a split pin of this type can have catastrophic results, possibly not immediately but at some future time when the nut has become sufficiently loosened that the elements can become disassembled leading to various failures of the assembly.

Without dissassembling and reassembling all of the parts, all that can be done for an inspection is for visual inspection to be carried out to check that the assembly has been properly completed and that all of the split pins are in place. In some cases the split pins are inadvertently omitted during manufacture or reassembly and in other cases they can become damaged or broken during use.

While such an inspection is relatively simple when carried out with a simple assembly of parts where the nut and split pin are readily apparent, it will be appreciated that in many highly complex machines such as air craft there are a large number of such split pin and nut combinations at various different angles and orientations within the assembly, many of which can be directly observed from an inspection panel but others can be in an orientation or position where it is more difficult to observe.

At the present time the various parts are manufactured from steel or other suitable materials which is often the same material as the other elements of the assembly so that it is very difficult by visual observation to determine the distinction between the various parts. Visual inspection is therefore very difficult and can in many cases overlook the fact that a essential split pin is missing leading to catastrophic consequences.

SUMMARY OF THE INVENTION

It is one object of the present invention, therefore, to provide an improved combination of nut and associated locking pin which enables visual inspection to be carried out more effectively.

It is a second object of the present invention to provide an improved method of inspecting an assembly including such nut and locking pin arrangements.

According to the first aspect of the invention there is provided a combination of bolt member with a male screw thread, a nut with a female screw thread for cooperation with the male screw thread and a locking pin arranged to engage the nut and bolt member to hold the nut against rotation, the locking pin having an outer surface which has a visually distinctive color difference from that of the nut.

According to a second aspect of the invention is provided a method of inspecting an assembly including a plurality of elements, and a plurality of fasteners each for fastening one of the elements to a respective other one of the elements and comprising a male screw threaded member, a nut having a female screw thread cooperating with the member so as to be fastened on the member and a locking pin engaging the member and a nut to prevent an intended rotation of the nut, the method comprising forming the pins with an outer surface which has a visibly distinctive color difference from that of the associated nut and visually inspecting the assembly to locate those nuts from which the associated pin is inadvertently missing.

The invention for the first time therefore provides relatively straight forward but unique step of ensuring that the locking pins are immediately visually distinctive so that there absence can be readily discerned by simple visual inspection. This would enable for example an inspection to be carried out simply by counting the number of readily visually apparent split pins or locking pins in an assembly thus immediately enabling the conclusion to be drawn that the split pins are present and are properly located in the associated nut.

Preferably, the outer surface of the locking pin also has a visually distinctive color difference from that of the bolt member.

Preferably, the bolt member is of the type having a transverse hole therethrough and wherein the nut has a castellated outer surface so that the pin can pass through spaces between castellations on the nut and through the transverse hole to hold the nut against rotation.

Preferably, the pin comprises a split pin of the type having a pair of legs and a loop section coupling ends of the legs together with opposed ends of the legs being free for bending apart.

Preferably, the whole of the outer surface of the pin has said visually distinctive color difference.

Preferably, the pin has a coating of a material defining a bright color, of a fluorescent material or of a phosphorescent material.

With the foregoing in view, and other advantages as will become apparent to those skilled in the art to which this invention relates as this specification proceeds, the invention is herein described by reference to the accompanying drawings forming a part hereof, which includes a description of the best mode known to the application and of the preferred typical embodiment of the principles of the present invention, in which:

The use of locking pins or split pins and associated nuts is well known and no description will be provided here of the various different assemblies in which this type of device, can be used.

DETAILED DESCRIPTION

Figure 1:
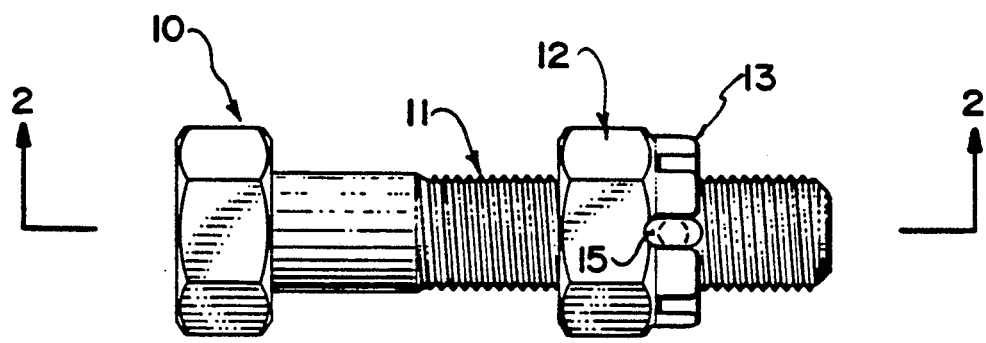
FIG. 1 is a top plan view of a nut, bolt member and locking pin combination.
Figure 2:
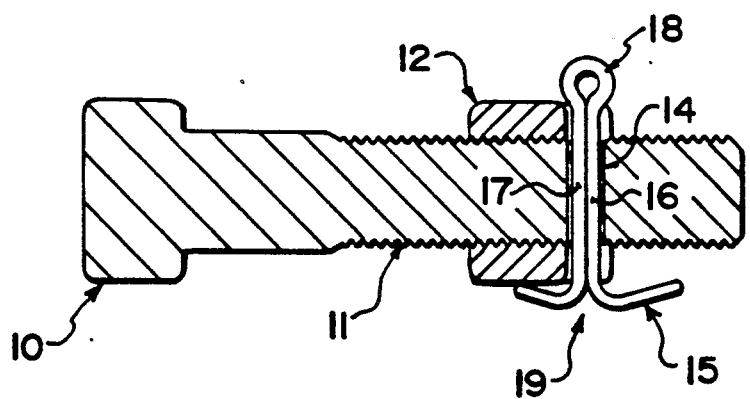
FIG. 2 is a cross section view along lines II—II of FIG. 1.

In FIGS. 1 and 2 is simply shown a bolt 10 with a screw threaded portion 11 associated with a nut 12 of the castellated type including projecting castellations 13. A hole 14 is provided in the screw threaded part of the bolt. A split pin 15 extends between the castellations and through the hole so that the nut cannot rotate on the screw threaded member for unloosening due to vibration.

The split pin is of the type including a pair of legs 16 and 17 indicated by a loop 18 at the upper end with lower ends of the legs being open so that they can be bent as indicated at 19 to prevent the pin being withdrawn through the hole.

In accordance with the present invention the pin has an outer layer which is formed so that it has a visually distinctive color difference from the remainder of the assembly and most particularly from the nut 12.

The visual distinctive difference can be obtained by forming the pin from material which is itself visually distinctive. Alternatively it can be applied by a coating of a brightly colored material for example a lacquer in various different colors distinctive from the generally metallic steel color used in the manufacture of the various elements of the assembly. The coating can also be phosphorescent or luminous if required.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

I claim:

1. A method of inspecting an assembly including a plurality of elements, and a plurality of fasteners, each for fastening one of the elements to a respective other one of the elements and comprising a male screw threaded member, a nut having a female screw thread cooperating with the member so as to be fastened on the member and a locking pin engaging the member and a nut to prevent an intended rotation of the nut, the method comprising forming the pins with an outer surface which has a visibly distinctive color difference from that of the associated nut and visually inspecting the assembly to locate those nuts from which the associated pin is inadvertently missing.

2. The invention according to claim 1 wherein the outer surface of the locking pin has a visually distinctive color difference from that of the bolt member.

3. The invention according to claim 1 wherein the bolt member has a transverse hole therethrough and wherein the nut has a castellated outer surface so that the pin can pass through spaces between castellations on the nut through the transverse hole to hold the nut against rotation.

4. The invention according to claim 1 wherein the pin comprises a split pin having a pair of legs and a loop section coupling ends of the legs together with opposed ends of the legs being free for bending apart.

5. The invention according to claim 1 wherein the whole of the outer surface of the pin has said visually distinctive color difference.

6. The invention according to claim 1 wherein the pin has a coating of a material defining a bright color.

7. The invention according to claim 1 wherein the pin has a coating of a fluorescent material.

8. The invention according to claim 1 wherein the pin has a coating of a phosphorescent material.

* * * * *